United States Patent [19]

Peery et al.

[11] Patent Number: 5,705,352
[45] Date of Patent: Jan. 6, 1998

[54] **MULTIPLE DRUG RESISTANCE GENE OF *ASPERGILLUS FUMIGATUS***

[75] Inventors: Robert B. Peery, Brownsburg; Paul L. Skatrud, Greenwood, both of Ind.

[73] Assignee: Eli Lilly and Company, Indianapolis, Ind.

[21] Appl. No.: 394,880

[22] Filed: Feb. 27, 1995

[51] Int. Cl.$^6$ .......................... G01N 33/53; G01N 33/569
[52] U.S. Cl. .............................................. 435/7.31; 435/6
[58] Field of Search ........................ 435/7.31, 6

[56] References Cited

U.S. PATENT DOCUMENTS

| | | | |
|---|---|---|---|
| 5,057,493 | 10/1991 | Takesako et al. | 514/11 |
| 5,158,876 | 10/1992 | Takesako et al. | 435/71.1 |
| 5,284,947 | 2/1994 | Kadam et al. | 544/245 |
| 5,399,483 | 3/1995 | Shibano et al. | 435/7.31 |
| 5,578,444 | 11/1996 | Edwards | 435/6 |
| 5,605,930 | 2/1997 | Samid | 514/510 |

FOREIGN PATENT DOCUMENTS

92/11034  7/1992  WIPO .

OTHER PUBLICATIONS

Dean, M. et al., yeast, Mar. 1994, vol. 10(3), pp. 377–383.
Kitahara, M. et al., Antimicrobial Agents & ChemoTherapy, Jun. 1976, pp. 908–914, vol. 9(6).
Kitahara, M. et al., Antimicrobial Agents & ChemoTherapy, Jun. 1976, pp. 915–919, vol. 9(6).
Tiligada, E. et al., 1993, Br. J. Pharmacol. 108:233.
Gottesman, M. and Pastan, I., Feb. 1983, TIPS 91:54–58.
Fojo, A. et al., 1987, Proc. Natl. Acad. Sci. USA 84:265–269.
Gottesman, M. and Pastan, I., 1993, Annu. Rev. Biochem. 62:385–427.
Pastan, I. and Gottesman, M., 1991, Annu. Rev. Med. 42:277–286.
Flier, J.S. and Underhill, L.H., 1987, New Eng. J. of Med. 316(22):1388–1393.
Gottesman, M. and Pastan, I., 1988, J. of Biol. Chem. 263(25): 12163–12166.
Raymond, M. et al., 1994, Mol. and Cell. Biol. 14(1):277–286.
Ruetz, S. et al., 1993, Proc. Natl. Acad. Sci. USA 90:11588–11592.
Raymond, M. et al., 1992, Science 256:232–234.
Nishi K., et al., 1992, Molecular Microbiology 6(6), 761–769.

*Primary Examiner*—James C. Housel
*Assistant Examiner*—Ginny Allen Portner
*Attorney, Agent, or Firm*—Thomas D. Webster; Thomas G. Plant; David E. Boone

[57] ABSTRACT

The invention provides isolated nucleic acid compounds encoding a multiple drug resistance protein of *Aspergillus fumigatus*. Vectors and transformed host cells comprising the multiple drug resistance-encoding DNA of *Aspergillus fumigatus* MDR-1 are also provided. The invention further provides assays which utilize these transformed host cells.

20 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2376 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION: 1..2376

( x i ) SEQUENCE DESCRIPTION: SEQ ID NO:1:

```
ATG CGC GGG ATT AGG TCG CTT CCC TGC TGG GCT CCT GGG TTG AGC ACG      48
Met Arg Gly Ile Arg Ser Leu Pro Cys Trp Ala Pro Gly Leu Ser Thr
 1               5                  10                  15

AAG CGA ATT CCT CCA CGA GAA CTG TTT GCA GAC CTA TTT CCT AAT GCC      96
Lys Arg Ile Pro Pro Arg Glu Leu Phe Ala Asp Leu Phe Pro Asn Ala
             20                  25                  30

TGC GTA ATT TCT GCG AGA CAC AGC GCT CGC AAT GGT CTC ATC CGA CAG     144
Cys Val Ile Ser Ala Arg His Ser Ala Arg Asn Gly Leu Ile Arg Gln
         35                  40                  45

TTT TCG GGT TGC TCC GGG TCA ATA AGC AAC AGT TGC AAC CCG CGT CCG     192
Phe Ser Gly Cys Ser Gly Ser Ile Ser Asn Ser Cys Asn Pro Arg Pro
     50                  55                  60

TAT CGA TCC GCA ATT ACG TCC TTG TTA TCC GCC AAT GTC TGT AGT AAA     240
Tyr Arg Ser Ala Ile Thr Ser Leu Leu Ser Ala Asn Val Cys Ser Lys
 65                  70                  75                  80

GGG GTT TCG GCC GTT CAA CCG CGA TTT TTG AGT ACA GTC AGG CTG TTT     288
Gly Val Ser Ala Val Gln Pro Arg Phe Leu Ser Thr Val Arg Leu Phe
                 85                  90                  95

TCT ACC TCC CAG CGA TCA TTG GAG CCA AAG TCG AAC GTC AAG TCG ACA     336
Ser Thr Ser Gln Arg Ser Leu Glu Pro Lys Ser Asn Val Lys Ser Thr
            100                 105                 110

GGC GGT CAG GTA GTG AGG CCA GAG TTA CAC CAG GAT CAG GAG CAT GAG     384
Gly Gly Gln Val Val Arg Pro Glu Leu His Gln Asp Gln Glu His Glu
        115                 120                 125

GAC ATC GAG AAA GGC TTT GAG CTA TCG GAG AGA GCC GCT CAG GCA GCA     432
Asp Ile Glu Lys Gly Phe Glu Leu Ser Glu Arg Ala Ala Gln Ala Ala
    130                 135                 140

CAG GTC AAC CTC AGC GCG AAG CTC GCC AAA GAC GGT GCT GCT GGA AAG     480
Gln Val Asn Leu Ser Ala Lys Leu Ala Lys Asp Gly Ala Ala Gly Lys
145                 150                 155                 160

AAG GCC GGG TTC AAG GAA ATA TGG AGG CTC TTA CTG ATT GCT CGA CCG     528
Lys Ala Gly Phe Lys Glu Ile Trp Arg Leu Leu Leu Ile Ala Arg Pro
                165                 170                 175

GAG GCG AAG AAG CTC GCC TTA GCC TTC CTT TTC TTG CTG GTA TCA TCT     576
Glu Ala Lys Lys Leu Ala Leu Ala Phe Leu Phe Leu Leu Val Ser Ser
            180                 185                 190

GGT ATT ACA ATG TCC ATC CCA TTT TCG ATT GGA AAG ATC ATG GAC ACC     624
Gly Ile Thr Met Ser Ile Pro Phe Ser Ile Gly Lys Ile Met Asp Thr
        195                 200                 205
```

| | | | | | | | | | | | | | | | | |
|---|---|---|---|---|---|---|---|---|---|---|---|---|---|---|---|---|
| TCG | ACA | AAA | GCG | ACT | ACA | GAA | GGT | GGT | AAT | GAG | CTC | TTT | GGT | CTG | AGC | 672 |
| Ser | Thr | Lys | Ala | Thr | Thr | Glu | Gly | Gly | Asn | Glu | Leu | Phe | Gly | Leu | Ser | |
| | 210 | | | | 215 | | | | | 220 | | | | | | |
| CTT | CCC | ATG | TTC | TAT | GGT | GCG | TTG | GCT | GGA | ATT | CTC | ACT | CTG | GGC | GCT | 720 |
| Leu | Pro | Met | Phe | Tyr | Gly | Ala | Leu | Ala | Gly | Ile | Leu | Thr | Leu | Gly | Ala | |
| 225 | | | | 230 | | | | | 235 | | | | | 240 | | |
| GCG | GCG | AAT | TAT | GGT | CGC | ATT | ATC | ATC | CTG | CGT | ATC | GTT | GGT | GAG | CGT | 768 |
| Ala | Ala | Asn | Tyr | Gly | Arg | Ile | Ile | Ile | Leu | Arg | Ile | Val | Gly | Glu | Arg | |
| | | | | 245 | | | | | 250 | | | | | 255 | | |
| ATT | GTT | GCC | AGA | CTT | CGC | TCG | AAG | CTC | TTC | CGC | CAG | ACA | TTT | GTG | CAA | 816 |
| Ile | Val | Ala | Arg | Leu | Arg | Ser | Lys | Leu | Phe | Arg | Gln | Thr | Phe | Val | Gln | |
| | | | 260 | | | | 265 | | | | | 270 | | | | |
| GAT | GCA | GAG | TTC | TTC | GAT | GCG | AAT | CGG | GTC | GGT | GAC | TTG | ATT | TCT | CGC | 864 |
| Asp | Ala | Glu | Phe | Phe | Asp | Ala | Asn | Arg | Val | Gly | Asp | Leu | Ile | Ser | Arg | |
| | | 275 | | | | | 280 | | | | | 285 | | | | |
| CTT | AGC | TCT | GAT | ACC | ATT | ATT | GTC | GGC | AAG | AGT | ATC | ACA | CAG | AAC | CTG | 912 |
| Leu | Ser | Ser | Asp | Thr | Ile | Ile | Val | Gly | Lys | Ser | Ile | Thr | Gln | Asn | Leu | |
| 290 | | | | | 295 | | | | | 300 | | | | | | |
| TCC | GAT | GGA | CTG | CGC | GCT | GCA | GTT | AGC | GGT | GCA | GCA | GGG | TTC | GGC | TTA | 960 |
| Ser | Asp | Gly | Leu | Arg | Ala | Ala | Val | Ser | Gly | Ala | Ala | Gly | Phe | Gly | Leu | |
| 305 | | | | 310 | | | | | 315 | | | | | 320 | | |
| ATG | GCC | TAC | GTC | AGT | CTC | AAG | CTC | TCC | AGT | ATA | CTG | GCT | CTC | CTT | CTC | 1008 |
| Met | Ala | Tyr | Val | Ser | Leu | Lys | Leu | Ser | Ser | Ile | Leu | Ala | Leu | Leu | Leu | |
| | | | | 325 | | | | | 330 | | | | | 335 | | |
| CCT | CCT | ATC | GGC | CTC | GGG | GCT | TTT | TTC | TAC | GGA | CGA | GCG | ATT | CGA | AAC | 1056 |
| Pro | Pro | Ile | Gly | Leu | Gly | Ala | Phe | Phe | Tyr | Gly | Arg | Ala | Ile | Arg | Asn | |
| | | | 340 | | | | | 345 | | | | | 350 | | | |
| CTG | AGT | CGT | CAA | ATC | CAG | AGG | AAT | CTT | GGG | ACC | TTG | ACT | AAG | ATT | GCG | 1104 |
| Leu | Ser | Arg | Gln | Ile | Gln | Arg | Asn | Leu | Gly | Thr | Leu | Thr | Lys | Ile | Ala | |
| | 355 | | | | | 360 | | | | | 365 | | | | | |
| GAG | GAG | CGC | CTA | GGC | AAC | GTC | AAG | ACT | AGC | CAG | TCC | TTT | GCT | GGC | GAG | 1152 |
| Glu | Glu | Arg | Leu | Gly | Asn | Val | Lys | Thr | Ser | Gln | Ser | Phe | Ala | Gly | Glu | |
| | 370 | | | | | 375 | | | | | 380 | | | | | |
| GTT | CTC | GAG | GTT | CGT | CGG | TAT | AAC | AAT | CAA | GTG | CGA | AAG | ATC | TTT | GAA | 1200 |
| Val | Leu | Glu | Val | Arg | Arg | Tyr | Asn | Asn | Gln | Val | Arg | Lys | Ile | Phe | Glu | |
| 385 | | | | | 390 | | | | | 395 | | | | | 400 | |
| CTT | GGC | AAA | AAA | GAA | TCC | CTT | ATC | AGT | GCC | ACA | TTC | TTT | AGC | TCC | ACC | 1248 |
| Leu | Gly | Lys | Lys | Glu | Ser | Leu | Ile | Ser | Ala | Thr | Phe | Phe | Ser | Ser | Thr | |
| | | | | 405 | | | | | 410 | | | | | 415 | | |
| GGG | TTT | GCT | GGC | AAC | ATG | ACC | ATC | CTG | GCA | TTG | CTG | TAC | GTC | GGA | GGA | 1296 |
| Gly | Phe | Ala | Gly | Asn | Met | Thr | Ile | Leu | Ala | Leu | Leu | Tyr | Val | Gly | Gly | |
| | | | 420 | | | | | 425 | | | | | 430 | | | |
| GGC | ATG | GTC | CAA | TCT | GGT | GCC | ATA | ACA | ATT | GGA | GAA | TTA | ACT | TCA | TTC | 1344 |
| Gly | Met | Val | Gln | Ser | Gly | Ala | Ile | Thr | Ile | Gly | Glu | Leu | Thr | Ser | Phe | |
| | | 435 | | | | | 440 | | | | | 445 | | | | |
| CTG | ATG | TAC | ACA | GCG | TAC | GCA | GGG | TCA | AGC | ATG | TTC | GGT | CTT | TCG | AGC | 1392 |
| Leu | Met | Tyr | Thr | Ala | Tyr | Ala | Gly | Ser | Ser | Met | Phe | Gly | Leu | Ser | Ser | |
| 450 | | | | | 455 | | | | | 460 | | | | | | |
| TTT | TAC | TCT | GAA | CTG | ATG | AAA | GGT | GTC | GGG | GCA | GCT | AGT | CGA | CTG | TTT | 1440 |
| Phe | Tyr | Ser | Glu | Leu | Met | Lys | Gly | Val | Gly | Ala | Ala | Ser | Arg | Leu | Phe | |
| 465 | | | | | 470 | | | | | 475 | | | | | 480 | |
| GAA | TTA | CAG | GAT | CGT | CAG | CCA | ACG | ATA | TCT | CCA | ACC | AAG | GGC | GAG | AAG | 1488 |
| Glu | Leu | Gln | Asp | Arg | Gln | Pro | Thr | Ile | Ser | Pro | Thr | Lys | Gly | Glu | Lys | |
| | | | | 485 | | | | | 490 | | | | | 495 | | |
| GTG | GCT | TCG | GCG | CGA | GGA | CCA | ATT | CGC | TTC | GAA | AAC | GTG | ACT | TTT | AGT | 1536 |
| Val | Ala | Ser | Ala | Arg | Gly | Pro | Ile | Arg | Phe | Glu | Asn | Val | Thr | Phe | Ser | |
| | | | 500 | | | | | 505 | | | | | 510 | | | |
| TAC | CCG | ACT | CGT | CCT | GCT | GTT | CCT | ATT | TTT | AGG | GAT | CTC | AAT | TTC | GAA | 1584 |
| Tyr | Pro | Thr | Arg | Pro | Ala | Val | Pro | Ile | Phe | Arg | Asp | Leu | Asn | Phe | Glu | |
| | | 515 | | | | | 520 | | | | | 525 | | | | |

| | | | | | | | | | | | | | | | | |
|---|---|---|---|---|---|---|---|---|---|---|---|---|---|---|---|---|
| ATT | CCC | CAA | GGG | ACC | AAT | GTT | GCT | ATC | GTT | GGG | CCC | TCA | GGA | GGT | GGA | 1632 |
| Ile | Pro 530 | Gln | Gly | Thr | Asn | Val 535 | Ala | Ile | Val | Gly | Pro 540 | Ser | Gly | Gly | Gly | |
| AAA | TCA | ACG | ATC | GCT | TCT | ATT | TTG | CTC | CGT | TTC | TAC | TCT | CCT | ACC | GAA | 1680 |
| Lys 545 | Ser | Thr | Ile | Ala | Ser 550 | Ile | Leu | Leu | Arg | Phe 555 | Tyr | Ser | Pro | Thr | Glu 560 | |
| GGA | AGA | GTT | CTC | ATC | GGT | GGC | AAA | GAC | ATC | ACC | CAT | ATG | AAC | GCC | AAA | 1728 |
| Gly | Arg | Val | Leu | Ile 565 | Gly | Gly | Lys | Asp | Ile 570 | Thr | His | Met | Asn | Ala 575 | Lys | |
| TCT | CTT | CGA | CGA | AAG | ATT | GGA | ATC | GTC | TCC | CAA | GAG | CCT | GTC | CTC | TTT | 1776 |
| Ser | Leu | Arg | Arg 580 | Lys | Ile | Gly | Ile | Val 585 | Ser | Gln | Glu | Pro | Val 590 | Leu | Phe | |
| TCG | GGG | ACT | ATA | GCG | GAG | AAC | ATT | GCG | TAT | GGT | AAA | CCT | CAG | GCC | AAG | 1824 |
| Ser | Gly | Thr 595 | Ile | Ala | Glu | Asn | Ile 600 | Ala | Tyr | Gly | Lys | Pro 605 | Gln | Ala | Lys | |
| CGG | TCA | GAG | ATC | GTT | GCA | GCT | GCG | CGC | AAG | GCG | AAC | TGC | CAG | TTC | ATA | 1872 |
| Arg | Ser 610 | Glu | Ile | Val | Ala | Ala 615 | Ala | Arg | Lys | Ala | Asn 620 | Cys | Gln | Phe | Ile | |
| AGT | GAC | TTT | CCG | GAT | GGT | CTT | GAC | ACC | CAG | GTC | GGA | CCC | CGG | GGC | GCT | 1920 |
| Ser | Asp 625 | Phe | Pro | Asp | Gly 630 | Leu | Asp | Thr | Gln | Val 635 | Gly | Pro | Arg | Gly | Ala 640 | |
| CAG | CTT | TCT | GGT | GGC | CAG | AAG | CAG | CGC | ATT | GCG | ATT | GCC | CGG | GCT | CTG | 1968 |
| Gln | Leu | Ser | Gly | Gly 645 | Gln | Lys | Gln | Arg | Ile 650 | Ala | Ile | Ala | Arg | Ala 655 | Leu | |
| ATC | AAG | GAT | CCT | GAT | ATT | CTC | ATA | CTC | GAT | GAA | GCA | ACT | TCT | GCT | CTC | 2016 |
| Ile | Lys | Asp | Pro 660 | Asp | Ile | Leu | Ile | Leu 665 | Asp | Glu | Ala | Thr | Ser 670 | Ala | Leu | |
| GAT | GCG | GAG | TCC | GAA | ACT | CTT | GTG | AAC | AGT | GCT | CTT | ACC | GCG | CTC | CTT | 2064 |
| Asp | Ala | Glu 675 | Ser | Glu | Thr | Leu | Val 680 | Asn | Ser | Ala | Leu | Thr 685 | Ala | Leu | Leu | |
| CGT | GGT | AAC | AAT | ACT | ACC | ATT | AGC | ATC | GCT | CAT | CGA | CTC | TCT | ACT | ATT | 2112 |
| Arg | Gly | Asn 690 | Asn | Thr | Thr | Ile | Ser 695 | Ile | Ala | His | Arg | Leu 700 | Ser | Thr | Ile | |
| AAG | AGA | TCC | GAT | ACG | ATT | ATT | GTC | CTT | GGT | CCC | GAC | GGA | AGA | GTA | GCC | 2160 |
| Lys 705 | Arg | Ser | Asp | Thr | Ile 710 | Ile | Val | Leu | Gly | Pro 715 | Asp | Gly | Arg | Val | Ala 720 | |
| GAA | CAA | GGC | AGT | TAT | GAG | GAG | CTC | AGT | GCT | CGC | CCT | GAT | GGC | GCC | TTC | 2208 |
| Glu | Gln | Gly | Ser | Tyr 725 | Glu | Glu | Leu | Ser | Ala 730 | Arg | Pro | Asp | Gly | Ala 735 | Phe | |
| ACC | AAA | TTG | ATG | GAG | TGG | CAG | ATG | AGC | GGC | GGT | GAG | GTG | ATG | GAC | CAG | 2256 |
| Thr | Lys | Leu | Met 740 | Glu | Trp | Gln | Met | Ser 745 | Gly | Gly | Glu | Val | Met 750 | Asp | Gln | |
| CTC | GCC | AAC | ACT | CCT | GCC | AAC | CCG | GTG | GCG | CAG | GAA | ACT | TCT | TGG | GAC | 2304 |
| Leu | Ala | Asn | Thr 755 | Pro | Ala | Asn | Pro 760 | Val | Ala | Gln | Glu | Thr 765 | Ser | Trp | Asp | |
| TTG | CAG | AGT | GAT | GAC | GGG | ACA | GAG | ATA | TCC | GAG | GAT | ACC | AAC | ATC | CCC | 2352 |
| Leu | Gln | Ser 770 | Asp | Asp | Gly | Thr | Glu 775 | Ile | Ser | Glu | Asp | Thr 780 | Asn | Ile | Pro | |
| TCA | GAG | CCG | CGA | AAA | ATT | GAT | TAG | | | | | | | | | 2376 |
| Ser 785 | Glu | Pro | Arg | Lys | Ile 790 | Asp | | | | | | | | | | |

( 2 ) INFORMATION FOR SEQ ID NO:2:

( i ) SEQUENCE CHARACTERISTICS:
        ( A ) LENGTH: 791 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

-continued

| | | | | | | | | | | | | | | | |
|---|---|---|---|---|---|---|---|---|---|---|---|---|---|---|---|
| Met | Arg | Gly | Ile | Arg | Ser | Leu | Pro | Cys | Trp | Ala | Pro | Gly | Leu | Ser | Thr |
| 1 | | | | 5 | | | | 10 | | | | | | 15 | |
| Lys | Arg | Ile | Pro | Pro | Arg | Glu | Leu | Phe | Ala | Asp | Leu | Phe | Pro | Asn | Ala |
| | | | 20 | | | | 25 | | | | | 30 | | | |
| Cys | Val | Ile | Ser | Ala | Arg | His | Ser | Ala | Arg | Asn | Gly | Leu | Ile | Arg | Gln |
| | | 35 | | | | | 40 | | | | | 45 | | | |
| Phe | Ser | Gly | Cys | Ser | Gly | Ser | Ile | Ser | Asn | Ser | Cys | Asn | Pro | Arg | Pro |
| | 50 | | | | 55 | | | | | | 60 | | | | |
| Tyr | Arg | Ser | Ala | Ile | Thr | Ser | Leu | Leu | Ser | Ala | Asn | Val | Cys | Ser | Lys |
| 65 | | | | | 70 | | | | 75 | | | | | | 80 |
| Gly | Val | Ser | Ala | Val | Gln | Pro | Arg | Phe | Leu | Ser | Thr | Val | Arg | Leu | Phe |
| | | | | 85 | | | | | 90 | | | | | 95 | |
| Ser | Thr | Ser | Gln | Arg | Ser | Leu | Glu | Pro | Lys | Ser | Asn | Val | Lys | Ser | Thr |
| | | | 100 | | | | | 105 | | | | | 110 | | |
| Gly | Gly | Gln | Val | Val | Arg | Pro | Glu | Leu | His | Gln | Asp | Gln | Glu | His | Glu |
| | | 115 | | | | | 120 | | | | | 125 | | | |
| Asp | Ile | Glu | Lys | Gly | Phe | Glu | Leu | Ser | Glu | Arg | Ala | Ala | Gln | Ala | Ala |
| | 130 | | | | | 135 | | | | | 140 | | | | |
| Gln | Val | Asn | Leu | Ser | Ala | Lys | Leu | Ala | Lys | Asp | Gly | Ala | Ala | Gly | Lys |
| 145 | | | | | 150 | | | | | 155 | | | | | 160 |
| Lys | Ala | Gly | Phe | Lys | Glu | Ile | Trp | Arg | Leu | Leu | Leu | Ile | Ala | Arg | Pro |
| | | | | 165 | | | | | 170 | | | | | 175 | |
| Glu | Ala | Lys | Lys | Leu | Ala | Leu | Ala | Phe | Leu | Phe | Leu | Leu | Val | Ser | Ser |
| | | | 180 | | | | | 185 | | | | | 190 | | |
| Gly | Ile | Thr | Met | Ser | Ile | Pro | Phe | Ser | Ile | Gly | Lys | Ile | Met | Asp | Thr |
| | | 195 | | | | | 200 | | | | | 205 | | | |
| Ser | Thr | Lys | Ala | Thr | Thr | Glu | Gly | Gly | Asn | Glu | Leu | Phe | Gly | Leu | Ser |
| | 210 | | | | | 215 | | | | | 220 | | | | |
| Leu | Pro | Met | Phe | Tyr | Gly | Ala | Leu | Ala | Gly | Ile | Leu | Thr | Leu | Gly | Ala |
| 225 | | | | | 230 | | | | | 235 | | | | | 240 |
| Ala | Ala | Asn | Tyr | Gly | Arg | Ile | Ile | Ile | Leu | Arg | Ile | Val | Gly | Glu | Arg |
| | | | | 245 | | | | | 250 | | | | | 255 | |
| Ile | Val | Ala | Arg | Leu | Arg | Ser | Lys | Leu | Phe | Arg | Gln | Thr | Phe | Val | Gln |
| | | | 260 | | | | | 265 | | | | | 270 | | |
| Asp | Ala | Glu | Phe | Phe | Asp | Ala | Asn | Arg | Val | Gly | Asp | Leu | Ile | Ser | Arg |
| | | | 275 | | | | | 280 | | | | | 285 | | |
| Leu | Ser | Ser | Asp | Thr | Ile | Ile | Val | Gly | Lys | Ser | Ile | Thr | Gln | Asn | Leu |
| | | 290 | | | | | 295 | | | | | 300 | | | |
| Ser | Asp | Gly | Leu | Arg | Ala | Ala | Val | Ser | Gly | Ala | Ala | Gly | Phe | Gly | Leu |
| 305 | | | | | 310 | | | | | 315 | | | | | 320 |
| Met | Ala | Tyr | Val | Ser | Leu | Lys | Leu | Ser | Ser | Ile | Leu | Ala | Leu | Leu | Leu |
| | | | | 325 | | | | | 330 | | | | | 335 | |
| Pro | Pro | Ile | Gly | Leu | Gly | Ala | Phe | Phe | Tyr | Gly | Arg | Ala | Ile | Arg | Asn |
| | | | 340 | | | | | 345 | | | | | 350 | | |
| Leu | Ser | Arg | Gln | Ile | Gln | Arg | Asn | Leu | Gly | Thr | Leu | Thr | Lys | Ile | Ala |
| | | 355 | | | | | 360 | | | | | 365 | | | |
| Glu | Glu | Arg | Leu | Gly | Asn | Val | Lys | Thr | Ser | Gln | Ser | Phe | Ala | Gly | Glu |
| | | 370 | | | | | 375 | | | | | 380 | | | |
| Val | Leu | Glu | Val | Arg | Arg | Tyr | Asn | Asn | Gln | Val | Arg | Lys | Ile | Phe | Glu |
| 385 | | | | | 390 | | | | | 395 | | | | | 400 |
| Leu | Gly | Lys | Lys | Glu | Ser | Leu | Ile | Ser | Ala | Thr | Phe | Phe | Ser | Ser | Thr |
| | | | | 405 | | | | | 410 | | | | | 415 | |
| Gly | Phe | Ala | Gly | Asn | Met | Thr | Ile | Leu | Ala | Leu | Leu | Tyr | Val | Gly | Gly |

|     |     |     | 420 |     |     |     | 425 |     |     |     | 430 |     |     |
| --- | --- | --- | --- | --- | --- | --- | --- | --- | --- | --- | --- | --- | --- |
| Gly | Met | Val | Gln | Ser | Gly | Ala | Ile | Thr | Ile | Gly | Glu | Leu | Thr | Ser | Phe |
|     |     | 435 |     |     |     |     | 440 |     |     |     |     | 445 |     |     |     |
| Leu | Met | Tyr | Thr | Ala | Tyr | Ala | Gly | Ser | Ser | Met | Phe | Gly | Leu | Ser | Ser |
|     | 450 |     |     |     |     | 455 |     |     |     |     | 460 |     |     |     |     |
| Phe | Tyr | Ser | Glu | Leu | Met | Lys | Gly | Val | Gly | Ala | Ala | Ser | Arg | Leu | Phe |
| 465 |     |     |     |     | 470 |     |     |     |     | 475 |     |     |     |     | 480 |
| Glu | Leu | Gln | Asp | Arg | Gln | Pro | Thr | Ile | Ser | Pro | Thr | Lys | Gly | Glu | Lys |
|     |     |     |     | 485 |     |     |     |     | 490 |     |     |     |     | 495 |     |
| Val | Ala | Ser | Ala | Arg | Gly | Pro | Ile | Arg | Phe | Glu | Asn | Val | Thr | Phe | Ser |
|     |     |     | 500 |     |     |     |     | 505 |     |     |     |     | 510 |     |     |
| Tyr | Pro | Thr | Arg | Pro | Ala | Val | Pro | Ile | Phe | Arg | Asp | Leu | Asn | Phe | Glu |
|     |     | 515 |     |     |     |     | 520 |     |     |     |     | 525 |     |     |     |
| Ile | Pro | Gln | Gly | Thr | Asn | Val | Ala | Ile | Val | Gly | Pro | Ser | Gly | Gly | Gly |
|     | 530 |     |     |     |     | 535 |     |     |     |     | 540 |     |     |     |     |
| Lys | Ser | Thr | Ile | Ala | Ser | Ile | Leu | Leu | Arg | Phe | Tyr | Ser | Pro | Thr | Glu |
| 545 |     |     |     |     | 550 |     |     |     |     | 555 |     |     |     |     | 560 |
| Gly | Arg | Val | Leu | Ile | Gly | Gly | Lys | Asp | Ile | Thr | His | Met | Asn | Ala | Lys |
|     |     |     |     | 565 |     |     |     |     | 570 |     |     |     |     | 575 |     |
| Ser | Leu | Arg | Arg | Lys | Ile | Gly | Ile | Val | Ser | Gln | Glu | Pro | Val | Leu | Phe |
|     |     |     | 580 |     |     |     |     | 585 |     |     |     |     | 590 |     |     |
| Ser | Gly | Thr | Ile | Ala | Glu | Asn | Ile | Ala | Tyr | Gly | Lys | Pro | Gln | Ala | Lys |
|     |     | 595 |     |     |     |     | 600 |     |     |     |     | 605 |     |     |     |
| Arg | Ser | Glu | Ile | Val | Ala | Ala | Ala | Arg | Lys | Ala | Asn | Cys | Gln | Phe | Ile |
|     | 610 |     |     |     |     | 615 |     |     |     |     | 620 |     |     |     |     |
| Ser | Asp | Phe | Pro | Asp | Gly | Leu | Asp | Thr | Gln | Val | Gly | Pro | Arg | Gly | Ala |
| 625 |     |     |     |     | 630 |     |     |     |     | 635 |     |     |     |     | 640 |
| Gln | Leu | Ser | Gly | Gly | Gln | Lys | Gln | Arg | Ile | Ala | Ile | Ala | Arg | Ala | Leu |
|     |     |     |     | 645 |     |     |     |     | 650 |     |     |     |     | 655 |     |
| Ile | Lys | Asp | Pro | Asp | Ile | Leu | Ile | Leu | Asp | Glu | Ala | Thr | Ser | Ala | Leu |
|     |     |     | 660 |     |     |     |     | 665 |     |     |     |     | 670 |     |     |
| Asp | Ala | Glu | Ser | Glu | Thr | Leu | Val | Asn | Ser | Ala | Leu | Thr | Ala | Leu | Leu |
|     |     | 675 |     |     |     |     | 680 |     |     |     |     | 685 |     |     |     |
| Arg | Gly | Asn | Asn | Thr | Thr | Ile | Ser | Ile | Ala | His | Arg | Leu | Ser | Thr | Ile |
|     | 690 |     |     |     |     | 695 |     |     |     |     | 700 |     |     |     |     |
| Lys | Arg | Ser | Asp | Thr | Ile | Ile | Val | Leu | Gly | Pro | Asp | Gly | Arg | Val | Ala |
| 705 |     |     |     |     | 710 |     |     |     |     | 715 |     |     |     |     | 720 |
| Glu | Gln | Gly | Ser | Tyr | Glu | Glu | Leu | Ser | Ala | Arg | Pro | Asp | Gly | Ala | Phe |
|     |     |     |     | 725 |     |     |     |     | 730 |     |     |     |     | 735 |     |
| Thr | Lys | Leu | Met | Glu | Trp | Gln | Met | Ser | Gly | Gly | Glu | Val | Met | Asp | Gln |
|     |     |     | 740 |     |     |     |     | 745 |     |     |     |     | 750 |     |     |
| Leu | Ala | Asn | Thr | Pro | Ala | Asn | Pro | Val | Ala | Gln | Glu | Thr | Ser | Trp | Asp |
|     |     | 755 |     |     |     |     | 760 |     |     |     |     | 765 |     |     |     |
| Leu | Gln | Ser | Asp | Asp | Gly | Thr | Glu | Ile | Ser | Glu | Asp | Thr | Asn | Ile | Pro |
|     | 770 |     |     |     |     | 775 |     |     |     |     | 780 |     |     |     |     |
| Ser | Glu | Pro | Arg | Lys | Ile | Asp |     |     |     |     |     |     |     |     |     |
| 785 |     |     |     |     | 790 |     |     |     |     |     |     |     |     |     |     |

MULTIPLE DRUG RESISTANCE GENE OF ASPERGILLUS FUMIGATUS

TECHNICAL FIELD OF THE INVENTION

This invention relates to recombinant DNA technology. In particular, the invention concerns the cloning of nucleic acid encoding a multiple drug resistance protein of *Aspergillus fumigatus*.

BACKGROUND OF THE INVENTION

Multiple drug resistance (MDR) mediated by the human mdr-1 gene product was initially recognized during the course of developing regimens for cancer chemotherapy (Fojo et al., 1987, *Journal of Clinical Oncology* 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leighmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, anti-arrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62:385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have been designed to discover anti-Candida compounds. During development of antifungal agents, activity has generally been optimized based on activity against *Candida albicans*. As a consequence, these anti-Candida compounds frequently do not possess clinically significant activity against other fungal species such as *Aspergillus fumigatus*. However, it is interesting to note that at higher concentrations some anti-Candida compounds are able to kill Aspergillus fungal species. This suggests that the antifungal target(s) of these anti-Candida compounds is present in Aspergillus as well. Such results indicate that Aspergillus may possess a natural mechanism of resistance that permits them to survive in clinically relevant concentrations of antifungal compounds. Until the present invention, such a general mechanism of resistance to antifungal compounds in *Aspergillus fumigatus* has remained undescribed.

SUMMARY OF THE INVENTION

The invention provides, inter alia, isolated nucleic acid molecules that comprise nucleic acid encoding a multiple drug resistance protein from *Aspergillus fumigatus*, known as Afu-MDR1, vectors encoding Afu-MDR1, and host cells transformed with these vectors.

In another embodiment, the invention provides a method for determining the fungal MDR inhibition activity of a compound which comprises:

a) growing a culture of yeast cells, transformed with a vector which provides expression of Afu-MDR1, in the presence of:

(i) an antifungal agent to which said yeast cell is resistant, but to which said yeast cell is sensitive in its untransformed state;

(ii) a compound suspected of possessing fungal MDR inhibition activity; and b) determining the fungal MDR inhibition activity of said compound by measuring the ability of the antifungal agent to inhibit the growth of said yeast cell.

BRIEF DESCRIPTION OF THE FIGURES

The restriction enzyme site and function maps presented in the accompanying drawings are approximate representations of cosmid pPSR-7 and plasmid pPSR-9, discussed herein. The restriction enzyme site information is not exhaustive. There may be more restriction enzyme sites of a given type on the vectors than actually shown on the maps.

DETAILED DESCRIPTION OF THE INVENTION

The present invention provides isolated nucleic acid molecules that comprise a nucleic acid sequence encoding Afu-MDR1. The amino acid sequence of Afu-MDR1 is provided in the Sequence Listing as SEQ ID NO: 2. The cDNA (complementary deoxyribonucleic acid) sequence encoding Afu-MDR1 is provided in the Sequence Listing as SEQ ID NO: 1.

Those skilled in the art will recognize that the degenerate nature of the genetic code enables one to construct many different nucleic acid sequences that encode the amino acid sequence of SEQ ID NO: 2. The cDNA sequence depicted by SEQ ID NO: 1 is only one of many possible Afu-MDR1 encoding sequences. Consequently, the constructions described below and in the accompanying examples for the preferred nucleic acid molecules, vectors, and transformants of the invention are illustrative and are not intended to limit the scope of the invention.

All nucleotide and amino acid abbreviations used in this disclosure are those accepted by the United States Patent and Trademark Office as set forth in 37 C.F.R. §1.822(b)(1994).

The term "vector" refers to any autonomously replicating or integrating agent, including but not limited to plasmids, cosmids, and viruses (including phage), comprising a nucleic acid molecule to which one or more additional nucleic acid molecules can be added. Included in the definition of "vector" is the term "expression vector". Vectors are used either to amplify and/or to express deoxyribonucleic acid (DNA), either genomic or cDNA, or RNA (ribonucleic acid) which encodes Afu-MDR1, or to amplify DNA or RNA that hybridizes with DNA or RNA encoding Afu-MDR1.

The term "expression vector" refers to vectors which comprise a transcriptional promoter (hereinafter "promoter") and other regulatory sequences positioned to drive expression of a DNA segment that encodes Afu-MDR1. Expression vectors of the present invention are replicable DNA constructs in which a DNA sequence encoding Afu-MDR1 is operably linked to suitable control sequences capable of effecting the expression of Afu-MDR1 in a suitable host. Such control sequences include a promoter, an optional operator sequence to control transcription, a sequence encoding suitable mRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, Afu-MDR1 may be synthesized by host cells transformed with vectors that provide for the expression of DNA encoding Afu-MDR1. The DNA encoding Afu-MDR1 may be the natural sequence or a synthetic sequence or a combination of both ("semi-synthetic sequence"). The in vitro or in vivo transcription and translation of these sequences results in the production of Afu-MDR1. Synthetic and semi-synthetic sequences encoding Afu-MDR1 may be constructed by techniques well known in the art. See Brown et al. (1979) *Methods in Enzymology*, Academic Press, N.Y., 68:109–151. Afu-MDR1-encoding DNA, or portions thereof, may be generated using a conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences may be constructed which encode Afu-MDR1. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al. *Molecular Cloning: A Laboratory Manual*, Cold Spring Harbor Press, Cold Spring Harbor Laboratory, Cold Spring Harbor, New York (1989), or *Current Protocols in Molecular Biology* (F. M. Ausbel et. al., 1989). The contents of both of these references are incorporated herein by reference.

Figure 1:
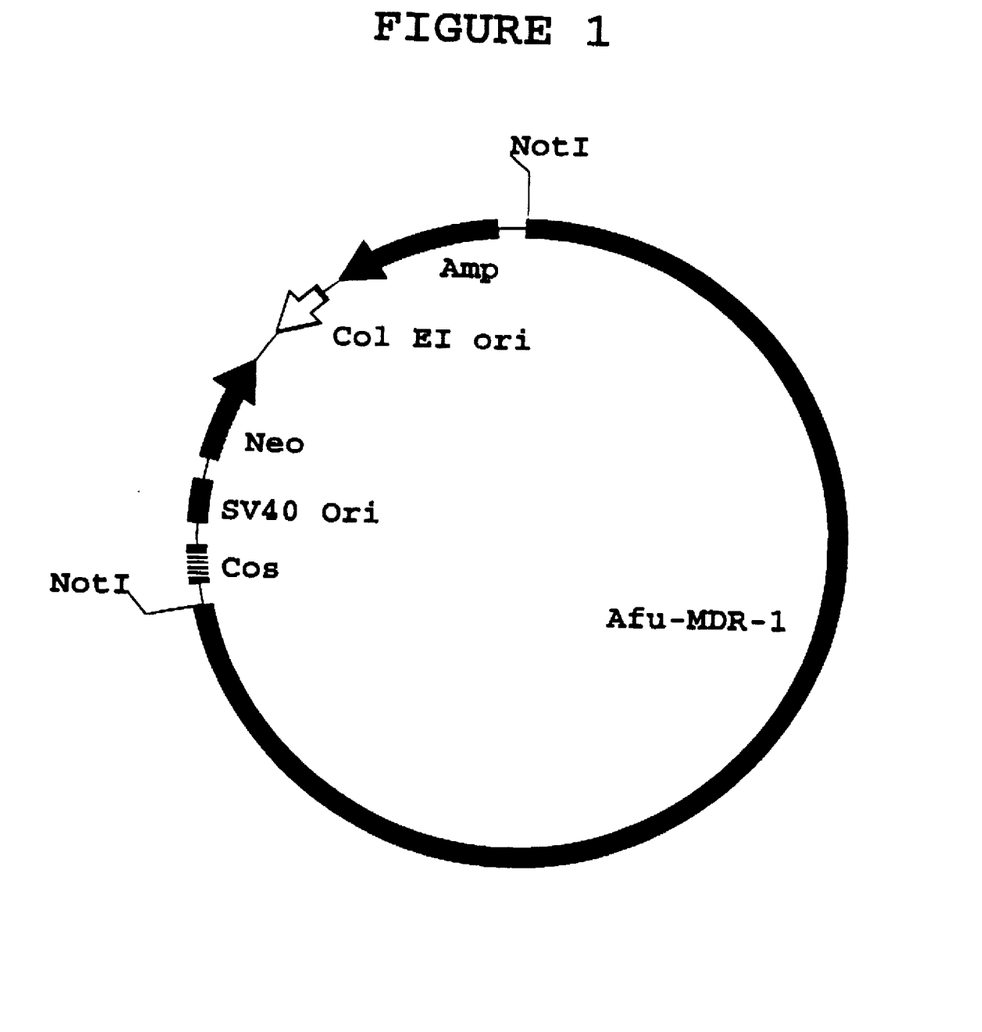
FIG. 1—A restriction enzyme site and function map of cosmid pPSR-7.

In another aspect, this invention provides the genomic DNA encoding the Afu-MDR1. This DNA sequence is preferably obtained from cosmid pPSR-7. Cosmid pPSR-7 can be obtained from the host cell *Escherichia coli* XL1-Blue/pPSR-7 which was deposited in the permanent culture collection of the Northern Regional Research Laboratory (NRRL), United States Department of Agriculture Service, 1815 North University Street, Peoria, Ill. 61604, on Feb. 10, 1995, and is available under accession number NRRL B-21407. A restriction site and function map of cosmid pPSR-7 is provided as FIG. 1 of the drawings. Cosmid pPSR-7 comprises the ColE1 origin of replication (ColE1) which allows replication in *E. coli* host cells, and the ampicillin resistance gene (Amp) for selection of *E. coli* cells transformed with the cosmid grown in the presence of ampicillin. The cosmid further comprises the cos site (cos) from bacteriophage lambda, the neomycin resistance gene and the SV40 origin of replication. The genomic DNA encoding Afu-MDR1 can be obtained from cosmid pPSR-7 on adjacent approximately 5.5 kilobase pair XbaI and 3.5 kilobase pair XbaI restriction enzyme fragments.

Examination of the genomic DNA sequence encoding Afu-MDR1 suggested the presence of introns. The precise location of suspected introns was determined by comparing the cDNA sequence encoding Afu-MDR1 to the sequence of the genomic DNA encoding Afu-MDR1. The cDNA sequence was obtained in the following manner. Messenger RNA (mRNA) isolated from *Aspergillus fumigatus* was converted to cDNA by conventional methodologies. Polymerase Chain Reaction (PCR) primers were designed to amplify regions of the gene encoding Afu-MDR1 suspected to contain introns. These regions were amplified from Afu-MDR1 encoding cDNA using standard PCR methodologies. The PCR fragments generated from Afu-MDR1 encoding cDNA were subcloned into the vector pCRScript$^{TM}$ (Stratagene, Inc.). The DNA sequence of the subcloned DNA was determined using the dideoxy sequencing method. The cDNA sequence, which lacks introns, was then compared to the genomic DNA sequence to locate the precise position of the introns in the genomic DNA.

To effect the translation of Afu-MDR1 encoding DNA, one inserts the natural, synthetic, or semi-synthetic Afu-MDR1-encoding DNA sequence into any of a large number of appropriate expression vectors through the use of appropriate restriction endonucleases and DNA ligases. Synthetic and semi-synthetic Afu-MDR1 encoding DNA sequences can be designed, and natural Afu-MDR1 encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the Afu-MDR1 encoding DNA with the control sequences to achieve proper in-frame transcription and translation of the Afu-MDR1 molecule. The Afu-MDR1 encoding DNA must be positioned so as to be in proper reading frame with the promoter and ribosome binding site of the expression vector, both of which are functional in the host cell in which Afu-MDR1 is to be expressed.

Expression of Afu-MDR1 in yeast cells, such as *Saccharomyces cerevisiae* is preferred. Suitable promoter sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHc-GAPC1 ATCC 57090, 57091), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose utilization (GAL1 found on plasmid pRY121 ATCC 37658 and on plasmid pPSR-9, described below). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYC1 promoter on plasmid YEpsec—hIIbeta, ATCC 67024), also are advantageously used with yeast promoters.

A variety of expression vectors useful in the present invention are well known in the art. For expression in Saccharomyces, the plasmid YRp7, for example, (ATCC-40053, Stinchcomb, et al., 1979, *Nature* 282:39; Kingsman et al., 1979, *Gene* 7:141; Tschemper et al., 1980, *Gene* 10:157) is commonly used. This plasmid contains the trp gene which provides a selection marker for a mutant strain of yeast lacking the ability to grow in tryptophan, for example ATCC no. 44076 or PEP4-1 (Jones, 1977, *Genetics* 85:12).

Expression vectors useful in the expression of Afu-MDR1 can be constructed by a number of methods. For example, the cDNA sequence encoding Afu-MDR1 can be synthesized using DNA synthesis techniques such as those described above. Such synthetic DNA can be synthesized to contain cohesive ends that allow facile cloning into an appropriately digested expression vector. For example, the cDNA encoding Afu-MDR1 can be synthesized to contain NotI cohesive ends. Such a synthetic DNA fragment can be ligated into a NotI-digested expression vector such as pYES-2 (Invitrogen Corp., San Diego Calif. 92121). The resultant plasmid is designated herein as pPSR-9. Plasmid pPSR-9 is useful for the expression of the Afu-MDR1 in *Saccharomyces cerevisiae*.

Plasmid pPSR-9 can also be constructed in the following manner. Logarithmic phase *Aspergillus fumigatus* mycelia are disrupted by grinding under liquid nitrogen according to the procedure of Minuth et al., 1982 (Current Genetics 5:227–231). *Aspergillus fumigatus* mRNA is preferably isolated from the disrupted mycelia using the QuickPrep™ mRNA Purification Kit (Pharmacia Biotech) according to the instructions of the manufacturer. cDNA is produced from the isolated mRNA using the TimeSaver® DNA Synthesis Kit (Pharmacia Biotech) using oligo (dT) according to the procedure described by the manufacturer. In this process an EcoRI/NotI adapter (Stratagene, Inc.) is ligated to each end of the double stranded cDNA. The adapter modified cDNA is ligated into the vector Lambda Zap$^R$II using the Predigested Lambda Zap$^R$II/EcoRI/CIAP Cloning Kit (Stratagene, Inc.) according to the instructions of the manufacturer to create a cDNA library.

The library is screened for full-length cDNA encoding Afu-MDR1 using a 32P-radiolabeled fragment of the Afu-MDR1 gene. This radiolabeled fragment is produced from the Afu-MDR1 genomic DNA present in cosmid DPSR-7. Utilizing the polymerase chain reaction (Gene Amp® Kit, Perkin Elmer Cetus, Norwalk, Conn.) and the following primers: 5'-AGCGATTCGAAACCTGAGTCG-3'(SEQ. I D. No: 3); and 5'-TCGTTGATTTTCCACCTCCTG-3'(SEQ. ID. No: 4), a Afu-MDR1 radiolabeled fragment is obtained. This radiolabeled fragment is used to probe the Aspergillus fumigatus cDNA library using standard hybridization techniques (Maniatis et al. 1992). In this manner, a full-length cDNA clone is recovered from the *Aspergillus fumigatus* cDNA library. A full-length cDNA clone recovered from the library is removed from the Lambda Zap$^R$II vector by digestion with the restriction endonuclease NotI which produces an approximately 2600 base pair DNA fragment encoding Afu-MDR1. The vector DNA fragment and the desired approximately 2600 base pair NotI DNA restriction fragment are separated by agarose gel electrophoresis. The desired approximately 2600 base pair NotI DNA fragment encoding Afu-MDR1 is isolated by cutting out that portion of the agarose gel containing the fragment and electroeluting the DNA using a Centrilutor™ Micro-electroeluter (Amicon, Inc.) according to the manufacturer's instructions. The isolated approximately 2600 base pair NotI restriction fragment encoding Afu-MDR1 is ligated to NotI digested pYES2 vector DNA. The correct orientation of the insert DNA is screened for by restriction endonuclease digestion using asymmetric sites located with the coding region and the flanking vector. The resultant plasmid, pPSR-9, is useful for the expression of the Afu-MDR1 in *Saccharomyces cerevisiae*.

Figure 2:
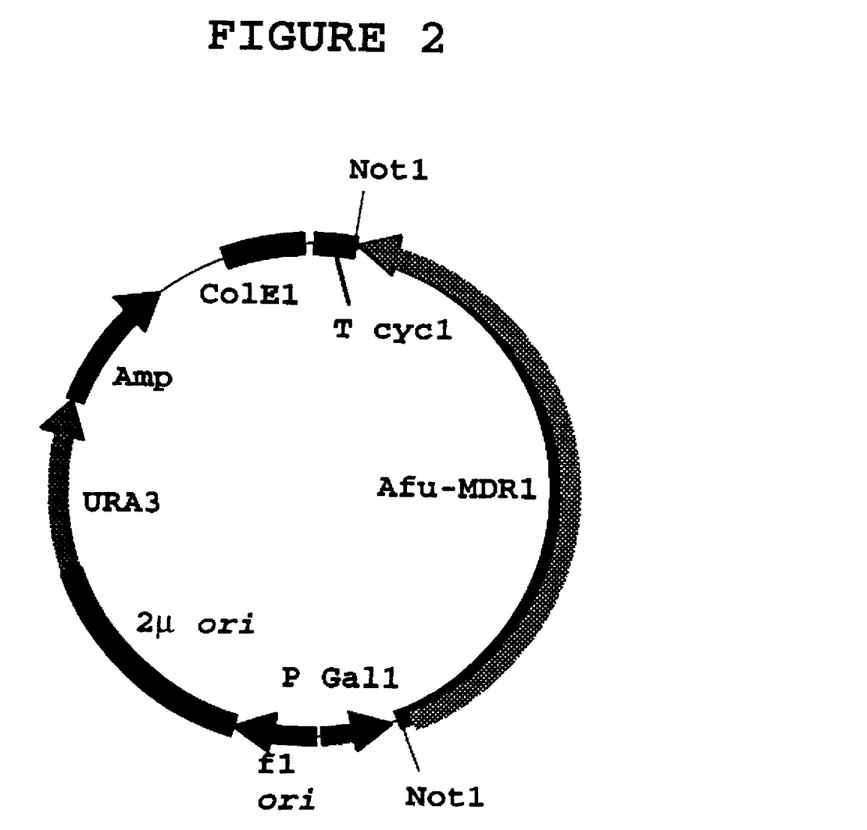
FIG. 2—A restriction enzyme site and function map of plasmid pPSR-9.

A representation of plasmid pPSR-9 is provided as FIG. 2. As noted above, this plasmid contains the Afu-MDR1 encoding DNA operably linked to the *Saccharomyces cerevisiae* GAL1 promoter (P Gal1). Plasmid pPSR-9 also comprises the yeast transcription terminator cyc1 (T cyc1) located in a position 3'to the Afu-MDR1 encoding DNA. Plasmid pPSR-9 further comprises the ColE1 origin of replication (ColE1) which allows replication in *Escherichia coli* host cells, and the ampicillin resistance gene (Amp) for selection of E. coli cells transformed with the plasmid and grown in the presence of ampicillin. Plasmid pPSR-9 further comprises the yeast 2μorigin of replication (2μori) allowing replication in yeast host cells, the yeast URA3 gene for selection of *S. cerevisiae* cells transformed with the plasmid grown in a medium lacking uracil, and the f1 origin of replication (f1 ori) from filamentous phage f1.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

Nucleic acid, either RNA or DNA, which encodes Afu-MDR1, or a portion thereof, is also useful in producing nucleic acid molecules useful in diagnostic assays for the detection of Afu-MDR1 mRNA, Afu-MDR1 cDNA, or Afu-MDR1 genomic DNA. Further, nucleic acid, either RNA or DNA, which does not encode Afu-MDR1, but which nonetheless is capable of hybridizing with Afu- MDR1-encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify Afu-MDR1 vectors and transformants and in in vitro diagnosis to detect Afu-MDR1-like mRNA, cDNA, or genomic DNA from other organisms.

U.S. Patent application Ser. No. 08/111680, the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with *Aspergillus fumigatus* MDR inhibition activity. Host cells that express Afu-MDR1 provide an excellent means for the identification of compounds useful as inhibitors of *Aspergillus fumigatus* MDR activity. Generally, the assay utilizes a culture of a yeast cell transformed with a vector which provides expression of Afu-MDR1. The expression of the Afu-MDR1 by the host cell enables the host cell to grow in the presence of an antifungal compound to which the yeast cell is sensitive to in the untransformed state. Thus, the transformed yeast cell culture is grown in the presence of i) an antifungal agent to which the untransformed yeast cell is sensitive, but to which the transformed host cell is resistant, and ii) a compound that is suspected of being an *Aspergillus fumigatus* MDR inhibitor. The effect of the suspected MDR inhibitor is measured by testing for the ability of the antifungal compound to inhibit the growth of the transformed yeast cell. Such inhibition will occur if the suspected *Aspergillus fumigatus* MDR inhibitor blocks the ability of the Afu-MDR1 to prevent the antifungal compound from acting on the yeast cell. An illustrative example of such an assay is provided in Example 3.

In order to illustrate more fully the operation of this invention, the following examples are provided, but are not to be construed as a limitation on the scope of the invention.

EXAMPLE 1

Source Of the MDR encoding Genomic DNA of *Aspergillus fumigatus*

Isolation of Cosmid pPSR-7

A lyophil of *Escherichia coli* XL1-Blue/pPSR-7 can be obtained from the Northern Regional Research Laboratories (NRRL), Peoria, Ill. 61604, under the accession number NRRL B-21407. Cosmid pPSR-7 may be isolated from NRRL B-21407 using techniques that are well-known to those skilled in the art. See Sambrook et al., *Molecular Cloning: A Laboratory Manual* (1988), Cold Spring Harbor Laboratory Press, Cold Spring Harbor, N.Y. or Ausubel et al., *Current Protocols in Molecular Biology* (1989), John Wiley & Sons, New York, N.Y. and supplements.

EXAMPLE 2

Expression of the Afu-MDR1 Protein

*Saccharomyces cerevisiae* INVSc1 cells (Invitrogen Corp., San Diego Calif. 92191) are transformed with the plasmid pPSR-9 by the technique described by J. D. Beggs, 1988, *Nature* 275:104–109). The transformed yeast cells are grown in a broth medium containing YNB/CSM-Ura/raf (YNB/CSM-Ura [Yeast Nitrogen Base (Difco Laboratories, Detroit, Mich.) supplemented with CSM-URA (Bio 101, Inc.)] supplemented with 4% raffinose) at 28° C. in a shaker incubator until the culture is saturated. To induce expression of the Afu-MDR1, a portion of the culture is used to inoculate a flask containing YNB/CSM-Ura medium supplemented with 2% galactose (YNB/CSM-Ura/gal) rather than raffinose as the sole carbon source. The inoculated flask is incubated at 28° C. for about 16 hours.

EXAMPLE 3

Antifungal Potentiator Assay

Approximately $1 \times 10^6$ cells of a *Saccharomyces cerevisiae* INVSc1/pPSR-9 culture are delivered to each of several agar plates containing YNB/CSM-Ura/gal. The agar surface is allowed to dry in a biohazard hood. *Saccharomyces cerevisiae* INVSc1/pPSR-9 cells express the Afu-MDR1 activity.

An antifungal compound that the untransformed yeast cell is typically sensitive to, such as R106I (U.S. Pat. No. 5,057,493, which is hereby incorporated herein by reference), is dissolved in 100% ethanol at a concentration of either 1 or 7 mg/ml. Twenty μl of the 1 mg/ml solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the *Saccharomyces cerevisiae* INVSc1/pPSR-9 cells.

Compounds to be tested for the ability to inhibit Afu-MDR1 are dissolved in dimethylsulfoxide (DMSO). The amount of compound added to the DMSO depends on the solubility of the individual compound to be tested. Twenty μl of the suspensions containing a compound to be tested are delivered to an antibiotic susceptibility test disc (Difco Laboratories, Detroit, Mich.). The disc is then placed on the surface of the dried petri plates containing the *Saccharomyces cerevisiae* INVSc1/pPSR-9 cells approximately 2 cm from the antifungal-containing disc. Petri plates containing the two discs are incubated at 28° C. for about 16–48 hours.

Following this incubation period, the petri plates are examined for zones of growth inhibition around the discs. A zone of growth inhibition near the antifungal disc on the test plate indicates that the compound being tested for MDR inhibition activity blocks the activity of Afu-MDR1 and allows the antifungal compound to inhibit the growth of the yeast host cell. Such compounds are said to possess MDR inhibition activity. Little or no zone of growth inhibition indicates that the test compound does not block MDR activity and, thus, the Afu-MDR1 is allowed to act upon the antifungal compound to prevent its activity upon the host cell.

We claim:

1. An isolated nucleic acid molecule that comprises nucleic acid encoding *Aspergillus fumigatus* MDR-1.

2. A nucleic acid molecule of claim 1 which is DNA.

3. The nucleic acid molecule of claim 2 that is SEQ. ID. No. 1.

4. The nucleic acid molecule of claim 1 that is genomic DNA.

5. A nucleic acid molecule of claim 1, which is labeled with a detectable moiety.

6. A nucleic acid molecule of claim 5 wherein the detectable moiety is selected from the group consisting of a fluorescent label, a radioactive atom, and a chemiluminescent label.

7. A vector comprising a nucleic acid of claim 1.
8. A vector comprising a nucleic acid of claim 2.
9. A vector comprising a nucleic acid of claim 3.
10. A vector comprising a nucleic acid of claim 4.
11. A host cell containing a vector of claim 7.
12. A host cell containing a vector of claim 8.
13. A host cell containing a vector of claim 9.
14. A host cell containing a vector of claim 10.
15. A host cell of claim 11 that is a yeast cell.
16. A host cell of claim 12 that is a yeast cell.
17. A host cell of claim 13 that is a yeast cell.
18. The host cell of claim 14 that is a yeast cell.
19. A method for determining the fungal MDR inhibition activity of a compound which comprises:

a) growing a culture of yeast cells, transformed with a vector which provides expression of the Afu-MDR-1, in the presence of:
  (i) an antifungal agent to which said yeast cell is resistant, but to which said yeast cell is sensitive in its untransformed state;
  (ii) a compound suspected of possessing *Aspergillus fumigatus* MDR inhibition activity; and
b) determining the fungal MDR inhibition activity of said compound by measuring the ability of the antifungal agent to inhibit the growth of said yeast cell.

20. A method of claim 19 wherein the yeast cell is *Saccharomyces cerevisiae*.

* * * * *